(12) United States Patent  
Serceki (10) Patent No.: US 7,787,014 B2
(45) Date of Patent: Aug. 31, 2010

(54) SYSTEMS, APPARATUS AND METHODS FOR PORTABLE IMAGING

(75) Inventor: Zeljko John Serceki, Hartland, WI (US)

(73) Assignee: General Electric Company, Schenectady, NY (US)

( * ) Notice: Subject to any disclaimer, the term of this patent is extended or adjusted under 35 U.S.C. 154(b) by 1090 days.

(21) Appl. No.: 11/312,682

(22) Filed: Dec. 19, 2005

(65) Prior Publication Data

US 2007/0140424 A1   Jun. 21, 2007

(51) Int. Cl.
*H04N 5/225* (2006.01)
*G01N 23/04* (2006.01)
*H04B 1/38* (2006.01)

(52) U.S. Cl. ............... 348/207.99; 348/207.1; 348/211.2; 348/211.3; 348/211.4; 378/62; 455/557

(58) Field of Classification Search ............ 348/207.99, 348/207.1, 211.2, 211.3, 211.4; 378/62; 455/557
See application file for complete search history.

(56) References Cited

U.S. PATENT DOCUMENTS

| | | | | |
|---|---|---|---|---|
| 5,708,840 | A * | 1/1998 | Kikinis et al. ............... 708/105 |
| 6,337,712 | B1 * | 1/2002 | Shiota et al. ............. 348/231.1 |
| 6,440,072 | B1 * | 8/2002 | Schuman et al. ............ 600/437 |
| 6,475,146 | B1 * | 11/2002 | Frelburger et al. .......... 600/437 |
| 6,833,867 | B1 * | 12/2004 | Anderson ................. 348/231.9 |
| 7,022,075 | B2 * | 4/2006 | Grunwald et al. ........... 600/446 |
| 2003/0078072 | A1 | 4/2003 | Serceki et al. |
| 2005/0136892 | A1 | 6/2005 | Oesterling et al. |
| 2005/0197093 | A1 * | 9/2005 | Wiklof et al. ............ 455/343.1 |
| 2006/0070384 | A1 * | 4/2006 | Ertel ............................ 62/3.3 |
| 2007/0004980 | A1 * | 1/2007 | Warner et al. ............... 600/411 |
| 2007/0180046 | A1 * | 8/2007 | Cheung et al. ............. 709/217 |
| 2007/0269010 | A1 * | 11/2007 | Turner ........................ 378/102 |

OTHER PUBLICATIONS

Broadcom press release # 659800, "Broadcom, HP and Linksys Make Wi-Fi Installation as Easy as Pushing a Button," printed Dec. 16, 2005.
Broadcom press release #682849, "Broadcom makes Wi-Fi Phone Installation as Easy as Pushing a Button," printed Dec. 16, 2005.

* cited by examiner

*Primary Examiner*—David L Ometz
*Assistant Examiner*—Quang V Le
(74) *Attorney, Agent, or Firm*—Peter Vogel, Esq.; William Baxter, Esq.; Michael G. Smith, Esq.

(57) ABSTRACT

In some implementations, a portable imaging system includes a host computer, a docking station connected to the host computer, and a portable imaging device intermittently attached to the docking station and configured to communicate data with the host computer through a wired connection when the portable imaging device is attached to the docking station, and through a wireless connection when detached from the docking station. In some implementations, a method for communicating data between a portable imaging device and a computer is also provided. In some implementations, the method includes determining whether a wired connection is established between the portable imaging device and the computer. In some implementations, if established, the wired connection is used to communicate data between the portable imaging device and the computer. In some implementations, if a wired connection is not established, a wireless connection between the portable imaging device and the computer is established and used to communicate data between the portable imaging device and the computer.

18 Claims, 6 Drawing Sheets

SYSTEMS, APPARATUS AND METHODS FOR PORTABLE IMAGING

FIELD OF THE INVENTION

This invention relates generally to medical imaging systems, and more particularly to techniques for using portable medical imaging devices.

BACKGROUND OF THE INVENTION

The increased portability of medical equipment, such as imaging devices, enables use of such equipment in a wider variety of situations and applications. For example, in emergency medical situations in the field, portable imaging devices are extremely useful. However, with an increase in portability, certain challenges arise relating to the management and use of such equipment, including power management challenges, data management challenges, wireless communication configuration challenges and storage challenges.

With regard to power management, portable imaging devices are typically battery-powered and, for practical purposes, are generally outfitted with a rechargeable battery. Due to the high power requirements of such devices, charging has to be conducted with regularity. Therefore, a user must remember to routinely connect the device to another power source to charge the batteries and maintain the device in an operable state. Monitoring power levels then becomes one challenge for a user of a portable imaging device.

With regard to data management, portable medical devices, such as portable imaging devices, generate large amounts of data. In a conventional imaging device, the data generated is typically transferred, via a wired connection, to a host computer system for processing and storage. By comparison, without a dedicated wired connection to a host computer, data transfer from a portable imaging device can present a challenge, especially when the data includes high-resolution images that are represented by large amounts of data and therefore are not easily transferred over a wireless connection.

With regard to wireless communication configuration, the portability of the device is typically dependent on the device being able to communicate with a host computer over a wireless connection. This communication requires that the device and the host computer share the same wireless configurations, which are routinely varied, i.e., changed or updated.

Finally, with regard to storage of the equipment when not in use, portable devices, due to their functional requirements, typically have awkward shapes and sizes. That combined with their fragile nature make them prone to damage if improperly placed or stored.

For the reasons stated above, and for other reasons stated below which will become apparent to those skilled in the art upon reading and understanding the present specification, there is a need in the art for improved techniques for using a portable imaging system.

BRIEF DESCRIPTION OF THE INVENTION

A portable imaging system is provided. The portable imaging system includes a host computer, a docking station connected to the host computer and a portable imaging device, e.g., a portable x-ray detector, intermittently attached to the docking station. The portable imaging device is configured to communicate data with the host computer through a wired connection when the portable imaging device is attached to the docking station, and through a wireless connection when the portable imaging device is detached from the docking station.

A method for communicating data between a portable imaging device and a computer includes determining whether a wired connection is established between the portable imaging device and the computer. If the wired connection is established, the wired connection is used to communicate data between the portable imaging device and the computer. If the wired connection is not established, a wireless connection is established between the portable imaging device and the computer and used to communicate data between the portable imaging device and the computer.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

Accordingly, a docking station 104 provides a convenient storage location for a portable x-ray detector 106 while simultaneously providing a direct, wired communications link to a host computer 102 and a power coupling to a power charging source for rechargeable batteries of portable x-ray detector 106. The direct communications link provided by docking station 104 between portable x-ray detector 106 and host computer 102 allows fast, efficient transfer of captured x-ray images from portable x-ray detector 106 to host computer 102 and direct, automatic and convenient communication of wireless communications configuration data from host computer 102 to portable x-ray detector 106. Thus, the needs for power management, data management, wireless communication configuration and storage techniques for portable imaging equipment are solved. As such, the present techniques provide for greater mobility of imaging equipment.

The detailed description is divided into five sections. In the first section, a system level overview is described. In the second section, apparatus of the system are described. In the third section, methods of using the apparatus are described. In the fourth section, the hardware and the operating environment in conjunction with which the present teachings may be practiced are described. Finally, in the fifth section, a conclusion of the detailed description is provided.

System Level Overview

Figure 1:
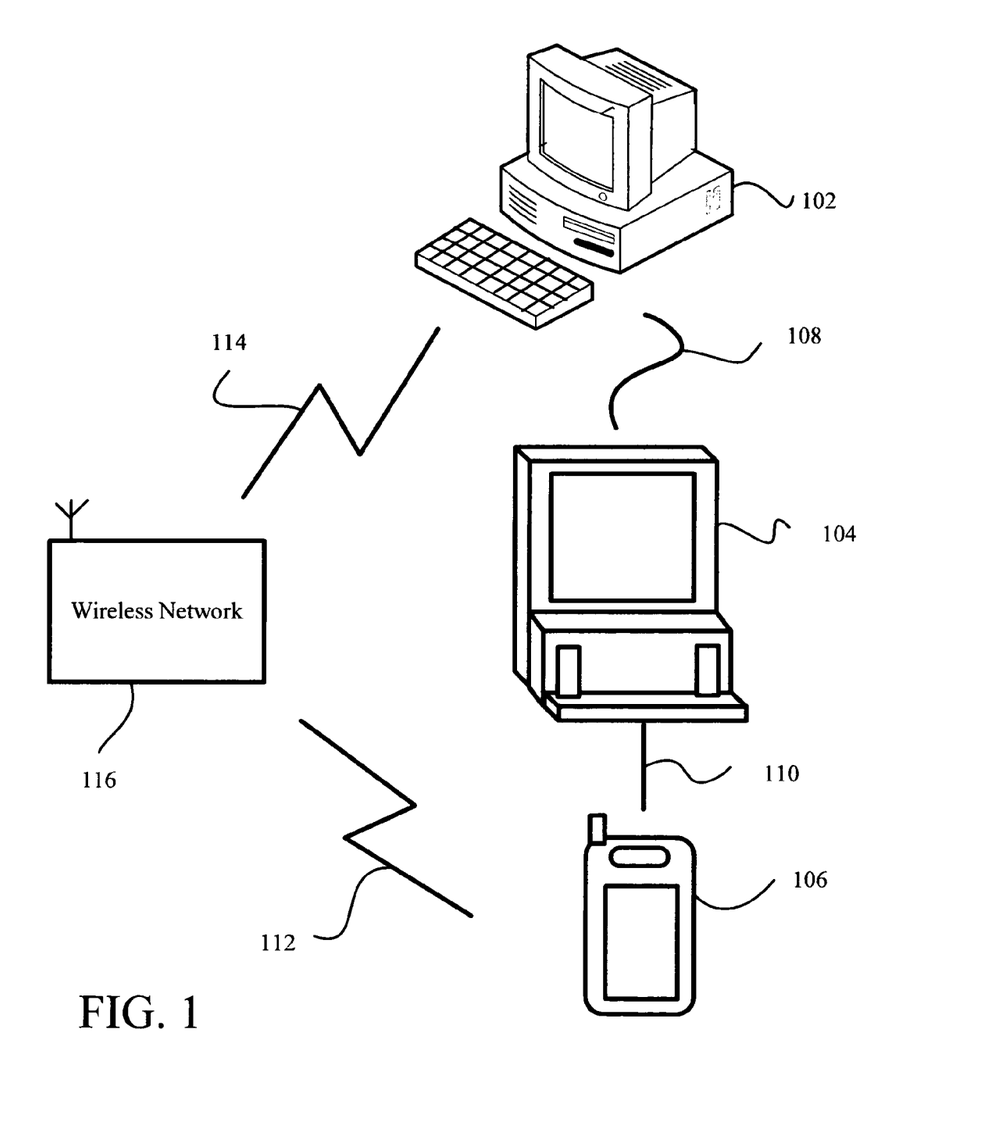
FIG. 1 is an overview diagram of an illustrative portable imaging system.

A system that solves the above-stated needs and thus provides greater mobility for imaging equipment is now described. FIG. 1 is an overview of illustrative portable imaging device system 100. System 100 includes host computer 102, docking station 104 and portable imaging device, e.g., portable x-ray detector 106. Host computer 102 is in communication with portable x-ray detector 106. The communication between host computer 102 and portable x-ray detector 106 can occur in one of two different modes.

In the first mode, a wired connection mode, portable x-ray detector 106 is "docked" at, e.g., in direct, wired connection 110 with, docking station 104. Host computer 102 is in communication with docking station 104 via wired connection 108 which can include, but is not limited to, a wired Ethernet® connection. Thus, according to this mode, portable x-ray detector 106 is in wired connection with host computer 102. This direct connection between host computer 102 and portable x-ray detector 106 via docking station 104 provides an efficient connection for data exchange between portable x-ray detector 106 and host computer 102, as well as, an efficient connection for the exchange of wireless configuration data between portable x-ray detector 106 and host computer 102. Further, the connection between docking station 104 and portable x-ray detector 106 can also provide a direct physical connection between a rechargeable power source of portable x-ray detector 106 and a charging power source.

In the second mode, a wireless connection mode, e.g., using wireless connections 112 and 114, portable x-ray detector 106 is detached from docking station 104. In this second mode, portable x-ray detector 106 communicates with host computer 102 through a wireless connection, e.g., through wireless network 116. Alternatively, portable x-ray detector 106 and host computer 102 can communicate directly to one another through an ad hoc wireless connection. A wireless connection can be advantageous in certain circumstances, as compared to a direct, wired connection, because the wireless connection provides for a greater mobility of the imaging equipment.

During normal operation of portable imaging device system 100, portable x-ray detector 106 is intermittently attached to docking station 104. Specifically, portable x-ray detector 106 is routinely attached to, and detached from, docking station 104.

An illustrative portable x-ray detector and docking station are described, for example, in conjunction with the description of FIGS. 2 and 3, respectively, below. The use of a portable x-ray detector and docking station is described, for example, in conjunction with the description of FIG. 5, below.

Apparatus Embodiments

Figure 2:
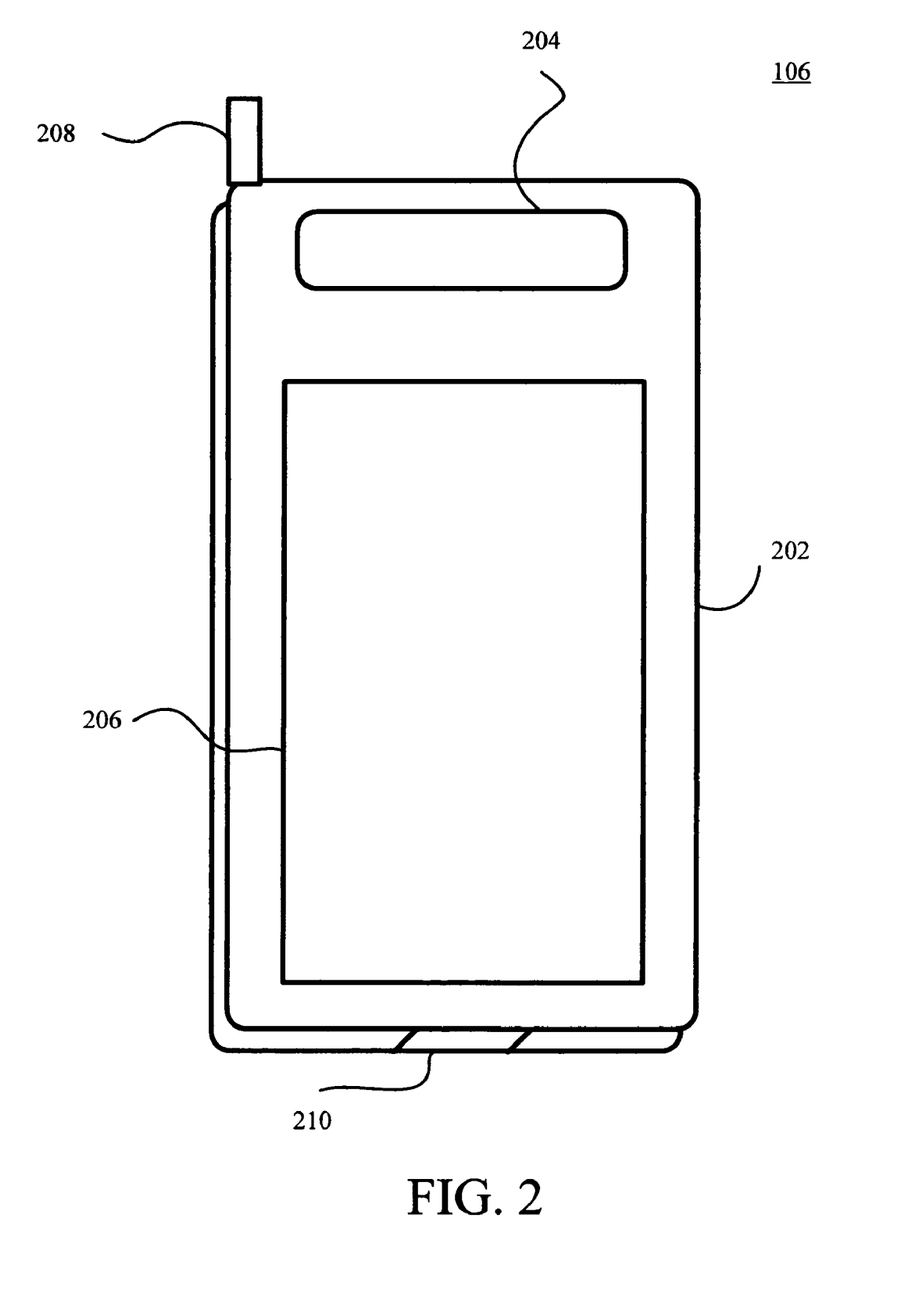
FIG. 2 is a diagram of an illustrative portable x-ray detector.

FIG. 2 is a diagram of illustrative portable x-ray detector 106. As described above, portable x-ray detector 106 is one component of portable imaging system 100. Portable x-ray detector 106 includes protective case 202, handle 204, digital x-ray detector element 206, antenna 208 and detector connection point 210.

Digital x-ray detector element 206 collects x-rays transmitted from an x-ray generator, e.g., through a subject (a patient), and converts the x-rays to an image including a number of pixels. Portable x-ray detector 106 then transfers this image to host computer 102, through either a wired connection via docking station 104, or through a wireless connection, e.g., using antenna 208, as described, for example, in conjunction with the description of FIG. 1, above. By way of example only, a digital x-ray detector element can be about 41 centimeters (cm) square and about one inch thick.

Portable x-ray detector 106 further includes a power source. Preferably, the power source is a rechargeable power source, such as a rechargeable battery (not shown), contained within protective case 202.

Detector connection point 210, along with a complementary mating connection point on docking station 104, which will be described below, form a direct connection between portable x-ray detector 106 and host computer 102 when portable x-ray detector 106 is attached to docking station 104. Further, in this illustrative embodiment in which the power source is a rechargeable battery, detector connection point 210 can also form a direct connection between portable x-ray detector 106 and a charging power source when portable x-ray detector 106 is attached to docking station 104. The charging of rechargeable batteries is well known and is not described further herein.

Figure 3:
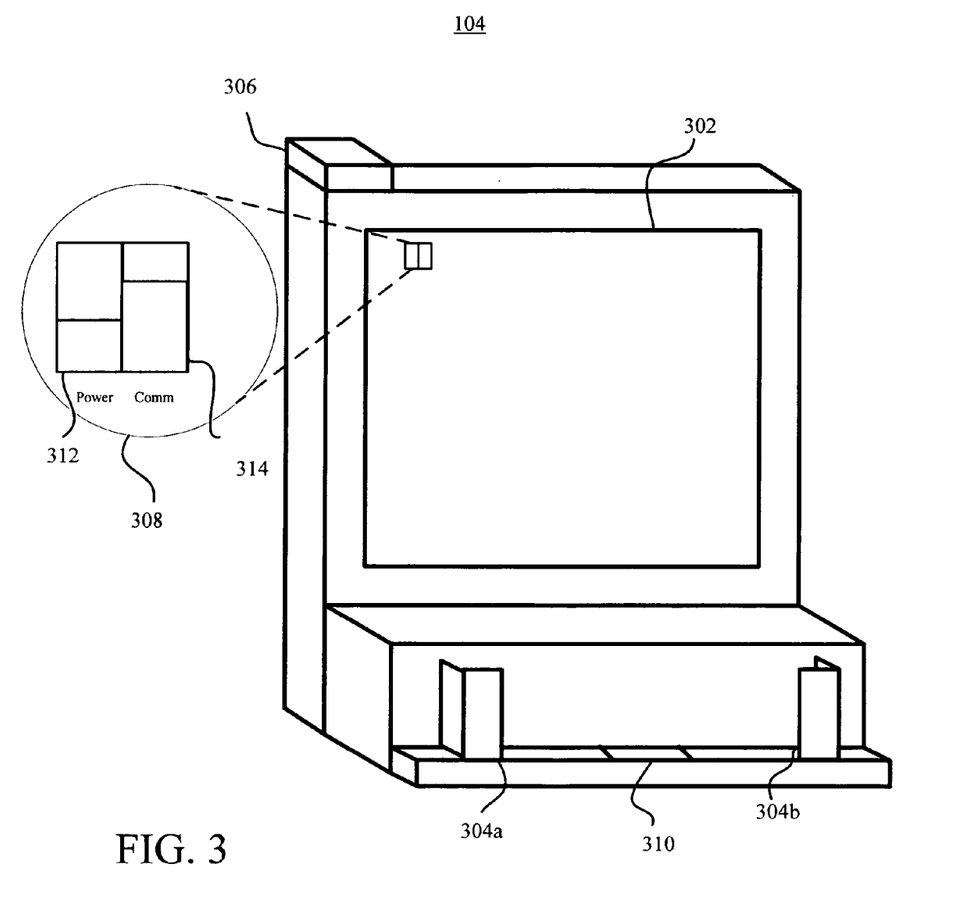
FIG. 3 is a diagram of an illustrative docking station.

FIG. 3 is a diagram of illustrative docking station 104. Docking station 104 is another component of portable imaging system 100. Docking station 104 includes display 302, portable x-ray detector attachment points 304a and 304b, user-activatable sensor 306 and docking station connection point 310.

Display 302 provides users with information about portable x-ray detector 106. For example, when portable x-ray detector 106 is attached to docking station 104, docking station 104 provides a wired data connection, as well as, a power charging connection, as described above. Display 302 shows power levels of the rechargeable power supply of portable x-ray detector 106 and indicates progress of data communication between portable x-ray detector 106 and host computer 102. Exemplary power level and communication progress indicia are shown in magnified view 308. By way of example only, in FIG. 3 power level indicium 312 is shown as a bar indicator that increases in height as the portable x-ray detector 106 power source charges. Similarly, communication progress indicium 314 is shown as a bar indicator that increases in height as more data is exchanged.

Figure 4:
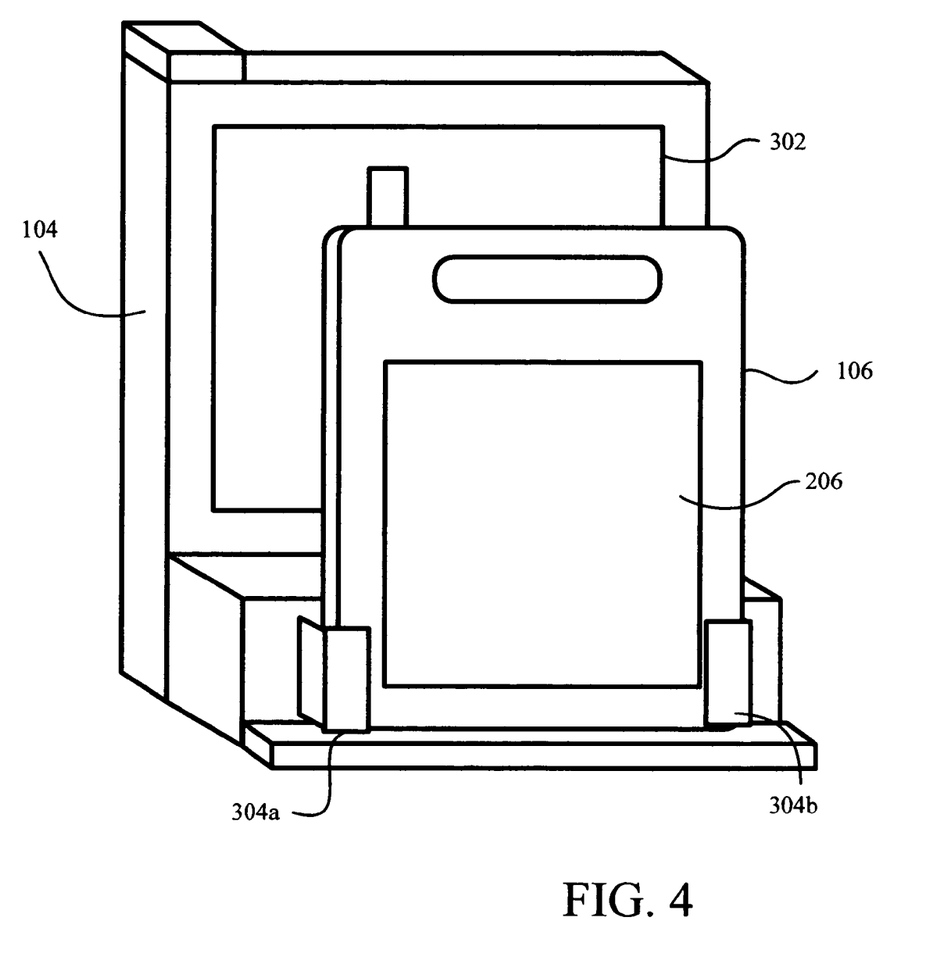
FIG. 4 is a diagram of an illustrative portable x-ray detector attached to a docking station.

Portable x-ray detector attachment points 304a and 304b are configured to physically retain and support portable x-ray detector 106 as shown in FIG. 4, for example. While the exemplary embodiment shown in FIG. 3 contains portable x-ray detector attachment points 304a and 304b for a single portable x-ray detector, it should be understood that the present teachings are not limited to the retention and attachment of a single portable x-ray detector. In other, alternative embodiments, multiple portable x-ray detectors can be attached to a single docking station at the same time.

Docking station connection point 310, along with complementary mating detector connection point 210 on portable x-ray detector 106, as described above, form a direct, wired connection between portable x-ray detector 106 and host computer 102 when portable x-ray detector 106 is attached to docking station 104. The connection formed between detector connection point 210 and docking station connection point 310 can include, but is not limited to, an RS-232 connection, a universal serial bus (USB) connection and an Ethernet® connection. RS-232 connections are the simplest of the aforementioned connections to implement, but provide the lowest data transfer rate.

User activation of user-activatable sensor 306 signals to host computer 102 that portable x-ray detector 106 will be removed from docking station 104 and, accordingly, that the direct, wired connection will be severed and subsequent wireless communication is expected. Therefore, in response, host computer 102 configures the operating parameters of expected wireless communications with portable x-ray detector 106 to enable portable x-ray detector 106 to communicate with host computer 102 wirelessly. Operating parameters relating to the wireless network connection shared between the portable x-ray detector and the host computer will be described in more detail below.

For proper wireless communication, host computer 102 sends operating parameters to portable x-ray detector 106 through the direct, wired connection prior to the direct, wired connection being severed. Therefore, docking station 104 can be configured to mechanically prevent detachment of portable x-ray detector 106 prior to completion of the sending of the operating parameters. For example, when the user presses user-activatable sensor 306 a locking mechanism can be activated that physically prevents portable x-ray detector 106 from being removed from docking station 104 until the sending is complete. Alternatively, the locking mechanism can be activated upon attachment of portable x-ray detector 106 to docking station 104. When the sending is complete, the locking mechanism is deactivated and portable x-ray detector 106 can be removed.

User-activatable sensor 306, as shown in FIG. 3, can be an "eject-type" button, that a user physically presses when the user wishes to remove portable x-ray detector 106 from docking station 104. Alternatively, other types of user-activatable sensors can be used instead of user-activatable sensor 306. By way of example only, the user-activatable sensor can be a graphical user interface (GUI) element represented in a portion of display 302. Thus, at least the portion of display 302 containing the user-activatable sensor can be touch-sensitive and perform the same functions described above with respect to user-activatable sensor 306.

Multiple user-activatable sensors may be employed on a single docking station. By way of example only, docking station 104 may have a button user-activatable sensor, as well as, a touch-sensitive sensor on the display. Each of these user-activatable sensors can be used independently of one another in that user activation of either user-activatable sensor initiates decoupling of portable x-ray detector 106 from docking station 104. In other words, a user can either press the button or touch the display prior to removing portable x-ray detector 106 from docking station 104.

Alternatively, the sending of the wireless operating parameters to portable x-ray detector 106 can be initiated when portable x-ray detector 106 is first attached to docking station 104. In this case, a user-activatable sensor is not needed to signal imminent detaching of portable x-ray detector 106. However, the user should take care not to remove portable x-ray detector 106 from docking station 104 until the configuration is complete, which under normal operating conditions takes no longer than about 0.5 seconds (s).

FIG. 4 is a diagram of illustrative portable x-ray detector 106 attached to docking station 104. As shown in FIG. 4, attachment points 304a and 304b of docking station 104 are configured to physically retain and support portable x-ray detector 106.

As described above, a direct, wired connection is made between portable x-ray detector 106 and host computer 102 through detector connection point 210 and docking station connection point 310. It is preferable that detector connection point 210 and docking station connection point 310 are symmetrical, such that portable x-ray detector 106 can be attached to docking station 104 in a number of different ways and still make a proper connection.

Symmetrical connection points include detector connection point 210 being centrally located on the mating surface of portable x-ray detector 106 (as shown in FIG. 2) and docking station connection point 310 being centrally located on the mating surface of docking station 104 (as shown in FIG. 3). For example, with the orientation shown in FIG. 4, wherein digital x-ray detector element 206 of portable x-ray detector 106 and display 302 of docking station 104 face the same direction, a connection would be made. Likewise, with an orientation wherein digital x-ray detector element 206 of portable x-ray detector 106 and display 302 of docking station 104 face each other (not shown), a proper connection is still also made.

As described above, if portable x-ray detector 106 is powered by a rechargeable battery, docking station 104 can provide a direct connection between portable x-ray detector 106 and a charging power source. The charging power source can derive its own power from an alternating current source, such as a standard wall outlet fed directly into docking station 104, for example. Alternatively, the recharging power source can derive its own power from host computer 102. For example, some wired connections include power connections. Examples include, but are not limited to, USB and Ethernet® connections through which host computer 102 can provide power to docking station 104 and therethrough to portable x-ray detector 106 for charging the rechargeable power source.

Method Embodiments

Figure 5:
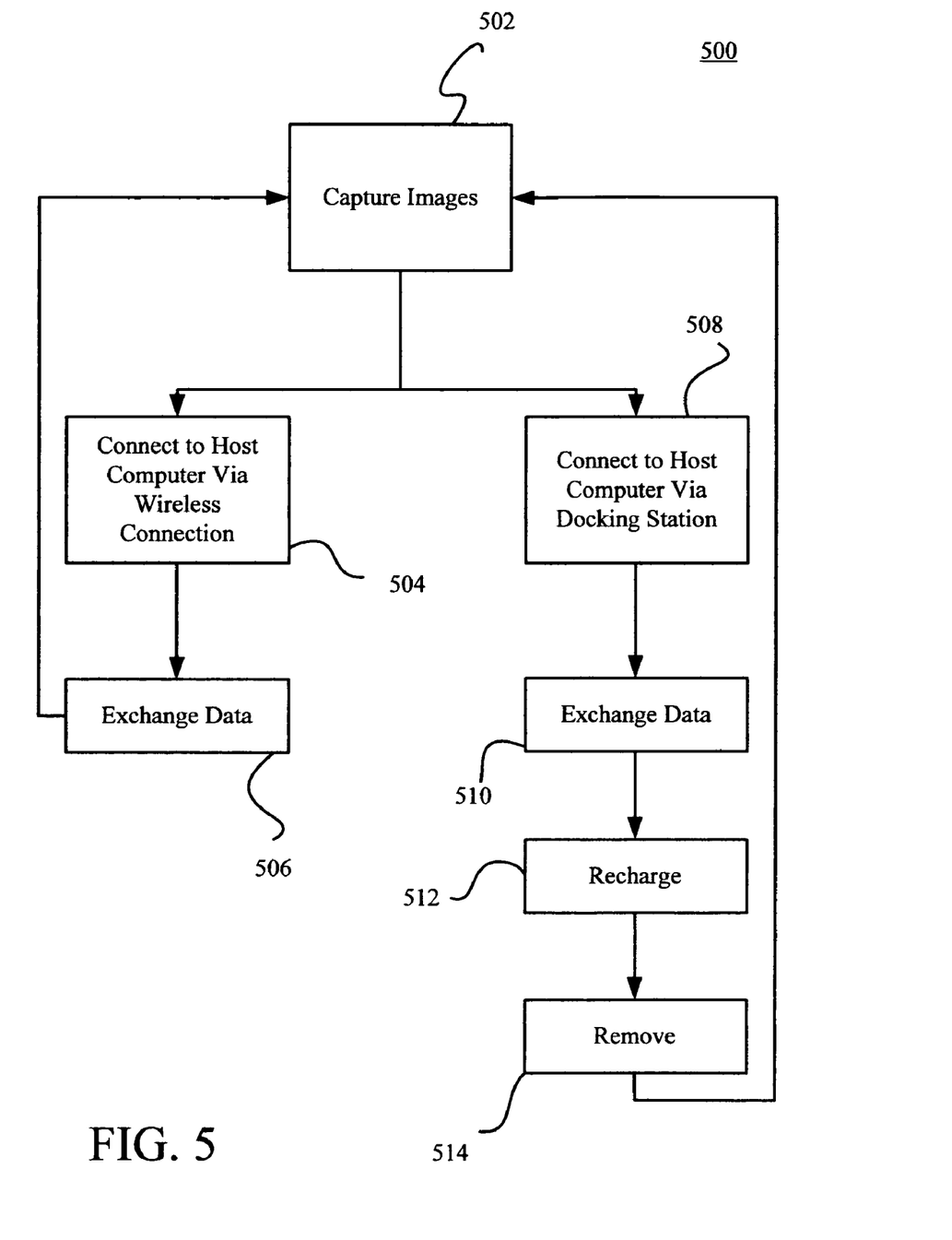
FIG. 5 is a flowchart of an illustrative methodology for using a portable imaging system.

FIG. 5 is a flowchart of illustrative methodology 500 for using portable x-ray detector 106. In step 502, portable x-ray detector 106 is used to capture images. Specifically, as described above, portable x-ray detector 106 collects x-rays from an x-ray generator that are passed through a subject, e.g., a patient, and converts the collected x-rays into an image of the subject.

Once the images are captured, portable x-ray detector 106 and host computer 102 cooperate to establish a connection therebetween. As described in conjunction with FIG. 1, this connection is made in one of two ways, either wirelessly in step 504 or through a direct, wired connection via docking station 104 connected to host computer 102 in step 508. In this illustrative embodiment, portable x-ray detector 106 initiates a wireless connection in step 504 whenever data is ready to send to host computer 102 and portable x-ray detector 106 fails to connect through detector connection point 210.

When the connection is wireless, data relating to the images captured, e.g., image data, as well as, data relating to the operating parameters of the wireless connection can be exchanged between host computer 102 and portable x-ray detector 106 in step 506.

When the connection is a direct connection made via docking station 104 connected to host computer 102, as in step 508, any of a number of functions may be performed. Namely, image data and operating parameter data can be exchanged between portable x-ray detector 106 and host computer 102 in step 510. The rechargeable power source of portable x-ray detector 106 can be charged in step 512. Once the desired functions are performed and at the convenience of the user, portable x-ray detector 106 can be removed from docking station 104 in step 514.

With regard to image data, the images captured by portable x-ray detector 106 typically include high-resolution images, for example, those images having an average size of about eight Mbytes, e.g., including 2048×2048 pixels at 16-bits per pixel. Using a wireless connection, the rate of transfer of these high-resolution images to host computer 102 is considerably slower than with a wired connection (for example, the current 802.11a technology can transfer data at a rate of 54 megabits per second (Mbps)) while current copper Ethernet® can transfer data at a rate of up to one (1) gigabit per second, i.e., nearly 200 times as fast. However, advances in wireless technology, for example, attaining wireless data transfer rates for an eight Mbyte of about two seconds, will make such wireless applications more practical.

In contrast, using the Ethernet® connection described above, an eight Mbyte image is transferred from portable x-ray detector 106 to host computer 102 in about 250 milliseconds (ms). Thus, for greater efficiency, the transfer of high-resolution images can be withheld during wireless data transfer, and saved in a memory of portable x-ray detector 106 (e.g., see FIG. 6, described below) until portable x-ray detector 106 is attached to docking station 104 and a direct, wired connection to host computer 102 is made. It is important to note that the data rate of the direct, wired connection depends upon the type of connection employed. For example USB1.1 has a raw data rate of 11 Mbps, whereas a 1200 baud RS-232 link is significantly slower. A 100BT Ethernet® link is almost ten times faster than USB1.0, but USB2.0 is almost five times faster than 100BT Ethernet®.

At least a portion of the operating parameter data exchanged between portable x-ray detector 106 and host computer 102 relates to the wireless connection that is shared between portable x-ray detector 106 and host computer 102 which can include, but is not limited to, operating frequency, encryption keys and network identification. For example, one operating parameter configures the wireless protocol being used. Namely, an 802.11 link can be established on a number of different channels with the 2.4 gigahertz (GHz) and 5.8 GHz bands. Host computer 102 can send configuration data to portable x-ray detector 106, causing portable x-ray detector 106 to communicate on a specific one of these channels. Additionally, if encryption is used, host computer 102 can send the keys to portable x-ray detector 106 to cause portable x-ray detector 106 to use those keys for secure communication.

When portable x-ray detector 106 includes a rechargeable battery and the connection to host computer 102 is made via docking station 104, a connection can also be made between the rechargeable battery and a charging power source in step 512. Alternatively, portable x-ray detector 106 can include a non-rechargeable power source, such as a disposable battery, obviating such charging.

Hardware and Operating Environment

Figure 6:
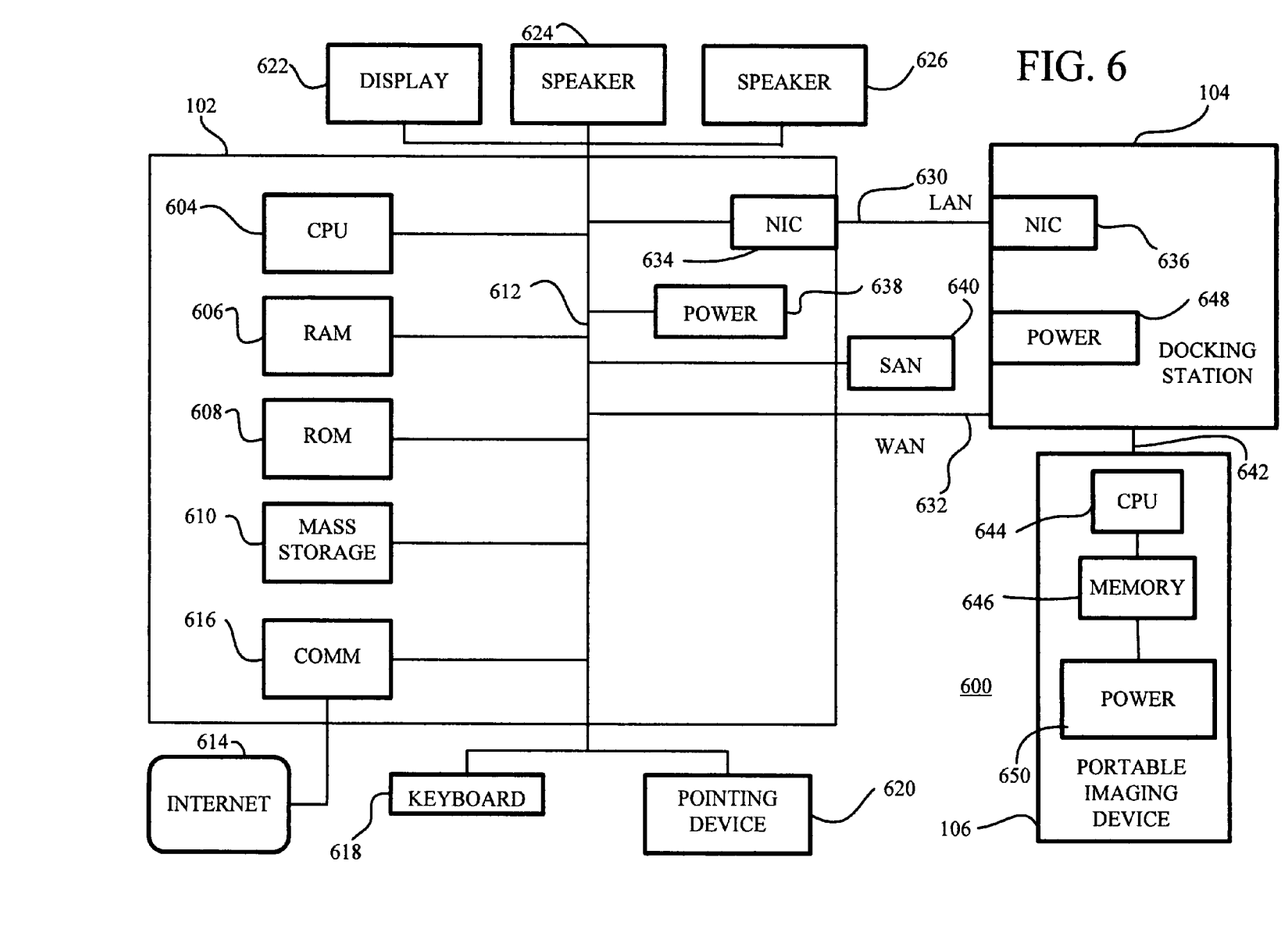
FIG. 6 is a block diagram of a hardware and operating environment in which different embodiments of the present teachings can be practiced.

FIG. 6 is a block diagram of hardware and operating environment 600 in which portable imaging can be practiced. The description of FIG. 6 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Host computer 102 includes a processor 604, commercially available from Intel, Motorola, Cyrix and others. Host computer 102 also includes random-access memory (RAM) 606, read-only memory (ROM) 608, and one or more mass storage devices 610, and a system bus 612, that operatively couples various system components to the processing unit 604. The memory 606, 608, and mass storage devices 610 are types of computer-accessible media. Mass storage devices 610 are more specifically types of nonvolatile computer-accessible media and can include one or more hard disk drives, floppy disk drives, optical disk drives, and/or tape cartridge drives. The processor 604 executes computer programs stored on the computer-accessible media.

Host computer 102 can be communicatively connected to the Internet 614 via a communication device 616. Internet 614 connectivity is well known within the art. In one embodiment, a communication device 616 is a modem that responds to communication drivers to connect to the Internet via what is known in the art as a "dial-up connection." In another embodiment, a communication device 616 is an Ethernet® or similar hardware network card connected to a local-area network (LAN) that itself is connected to the Internet via what is known in the art as a "direct connection" (e.g., T1 line, etc.).

A user enters commands and information into the host computer 102 through input devices such as a keyboard 618 or a pointing device 620. The keyboard 618 permits entry of textual information into host computer 102, as known within the art, and embodiments are not limited to any particular type of keyboard. Pointing device 620 permits the control of the screen pointer provided by a GUI of operating systems such as versions of Microsoft Windows®. Embodiments are not limited to any particular pointing device 620. Such pointing devices include mice, touch pads, trackballs, remote controls and point sticks. Other input devices (not shown) can include a microphone, joystick, game pad, satellite dish, scanner, or the like.

In some embodiments, host computer 102 is operatively coupled to a display device 622. Display device 622 is connected to the system bus 612. Display device 622 permits the display of information, including computer, video and other information, for viewing by a user of the computer. Embodiments are not limited to any particular display device 622. Such display devices include cathode ray tube (CRT) displays (monitors), as well as, flat panel displays such as liquid crystal displays (LCD's). In addition to a monitor, computers typically include other peripheral input/output devices such as printers (not shown). Speakers 624 and 626 provide audio output of signals. Speakers 624 and 626 are also connected to the system bus 612.

Host computer 102 also includes an operating system (not shown) that is stored on the computer-accessible media RAM 606, ROM 608, and mass storage device 610, and is executed by the processor 604. Examples of operating systems include Microsoft Windows®, Apple MacOS®, Linux®, UNIX®. Examples are not limited to any particular operating system, however, and the construction and use of such operating systems are well known within the art.

Embodiments of host computer 102 are not limited to any type of host computer 102. In varying embodiments, host computer 102 comprises a PC-compatible computer, a MacOS®-compatible computer, a Linux®-compatible computer, or a UNIX®-compatible computer. The construction and operation of such computers are well known within the art.

Host computer 102 can be operated using at least one operating system to provide a GUI including a user-controllable pointer. Host computer 102 can have at least one web browser application program executing within at least one operating system, to permit users of host computer 102 to access intranet or Internet world-wide-web pages as addressed by Universal Resource Locator (URL) addresses. Examples of browser application programs include Netscape Navigator® and Microsoft Internet Explorer®.

Host computer 102 can operate in a networked environment using logical connections to one or more remote computers, such as docking station 104. These logical connections are achieved by a communication device that is coupled to, or is a part of, the host computer 102. Embodiments are not limited to a particular type of communications device. Docking station 104 can be another computer, a client, a peer device or other common network node. The logical connections depicted in FIG. 6 include a local-area network (LAN) 630 and a wide-area network (WAN) 632. Such networking environments are commonplace in offices, enterprise-wide computer networks, intranets and the Internet.

When used in a LAN-networking environment, the host computer 102 and docking station 104 are connected to the local network 630 through network interface circuitry (NIC) 634 and 636. An NIC is one type of communications device 616. When used in a conventional WAN-networking environment, the host computer 102 and docking station 104 communicate with a WAN 632 through modems (not shown). The modem, which can be internal or external, is connected to the system bus 612. In a networked environment, program modules depicted relative to the host computer 102, or portions thereof, can be stored in the docking station 104.

One or more portable imaging devices such as portable x-ray detector 106 can be directly connected to docking station 104, through connection 642. As described above, connection 642 is made through detector connection point 210 and docking station connection point 310. Each of these portable imaging devices can include a CPU 644, e.g., for processing image data, and a memory 646, e.g., for storing image data, as shown in portable x-ray detector 106.

Host computer 102 includes power supply 638. Power supply 638 can be derived from an alternating current source, such as a standard wall outlet, or from a battery. Power supply 638 serves as a power source for host computer 102. Power supply 638 can also serve as a power source for docking station 104 and/or as a charging power source for portable x-ray detector 106, e.g., when LAN connection 630 includes a power connection.

Alternatively, docking station 104 can include power supply 648. Power supply 648 can be derived from an alternating current source, such as a standard wall outlet, or from battery. Power supply 648 serve as a charging power source for portable x-ray detector 106.

Portable x-ray detector 106 includes power supply 650. Power supply 650 can be derived from a rechargeable battery. When power supply 650 is derived from a rechargeable battery, the rechargeable battery can be charged using either of power supply 638 and power supply 648, through connection 642.

Conclusion

A portable imaging system, apparatus and methods of use have been described. Although specific embodiments are illustrated and described herein, any arrangement which is calculated to achieve the same purpose may be substituted for the specific embodiments shown. This application is intended to cover any adaptations or variations. For example, although described in medical imaging terms, it should be appreciated that implementations can be made in an industrial or any other secured environment that provides the required relationships.

In particular, the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. Embodiments are applicable to future medical devices, different imaging systems, and new data types.

The terminology used in this application with respect to the portable imaging technology is meant to include all data objects and network environments and alternate technologies that provide the same functionality as described herein.

I claim:

1. A portable imaging system comprising:
    a host computer;
    a docking station connected to the host computer; and
    at least one portable X-ray detector intermittently attached to the docking station, the at least one portable X-ray detector being configured to communicate data with the host computer through a wired connection when the at least one portable X-ray detector is attached to the docking station, and through a wireless connection when the at least one portable X-ray detector is detached from the docking station,
    wherein the data includes wireless communication configuration data, the wireless communication configuration data including operating frequency data, encryption key data and network identification data,
    wherein the docking station is configured to mechanically prevent detachment of at least one portable X-ray detector prior to completion of sending of the wireless communication configuration data through the wired connection.

2. The system of claim 1, wherein the docking station is connected to the host computer by a direct wired connection.

3. The system of claim 1, wherein the docking station physically retains and supports the at least one portable X-ray detector when the at least one portable X-ray detector is attached to the docking station.

4. The system of claim 1, wherein the communicated data further comprises image data.

5. The system of claim 1, wherein the docking station further comprises:
    an activatable sensor that is operable to signal the host computer that the at least one portable X-ray detector will be removed from the docking station and that a direct wired connection will be severed and subsequent wireless communication will be performed by the at least one portable X-ray detector.

6. The system of claim 5, wherein the docking station further comprises:
    a locking mechanism that can be activated to physically prevent the at least one portable x-ray detector from being removed from the docking station until sending of the wireless communication configuration data is complete.

7. The system of claim 1, activating a locking mechanism upon attachment of portable x-ray detector to a docking station.

8. A method for communicating data between a portable X-ray detector and a computer, the method comprising:
    determining whether a wired connection is established between the portable X-ray detector and the computer;
    upon a condition in which the wired connection is established, using the wired connection to communicate data between the portable X-ray detector and the computer,
    preventing mechanical detachment of the portable X-ray detector prior to completion of sending of the data; and
    upon a condition in which the wired connection is not established:
        establishing a wireless connection between the portable X-ray detector and the computer; and using the wireless connection to communicate data between the portable X-ray detector and the computer,
wherein the data includes wireless communication configuration data, the wireless communication configuration data including operating frequency data, encryption key data and network identification data.

9. The method of claim 8, further comprising:
upon the condition in which the wired connection is established, sending the wireless communication configuration data from the computer to the portable X-ray detector for subsequent use in the wireless connection.

10. The method of claim 9, further comprising:
signaling to the computer that the portable X-ray detector will be removed from a docking station that that the wired connection will be severed and subsequent wireless communication is expected.

11. The method of claim 8, further comprising:
upon the condition in which the wired connection is established, sending image data from the portable X-ray detector to the computer.

12. The method of claim 8, further comprising:
upon the condition in which the wired connection is established, accepting charging power for a rechargeable power supply in the portable X-ray detector.

13. The method of claim 8, wherein the computer is a host computer.

14. The method of claim 8, further comprising:
upon the condition in which the wired connection is established, signaling to the computer that the wired connection is going to be severed.

15. A computer-accessible medium storing executable instructions capable of directing a processor to perform:
determining whether a wired connection is established between a portable X-ray detector and the computer;
upon a condition in which the wired connection is established, using the wired connection to communicate data between the portable X-ray detector and the computer,
preventing mechanical detachment of the portable X-ray detector prior to completion of sending of the data; and
upon a condition in which the wired connection is not established:
establishing a wireless connection between the portable X-ray detector and the computer; and
using the wireless connection to communicate data between the portable X-ray detector and the computer,
wherein the data includes wireless communication configuration data, the wireless communication configuration data including operating frequency data, encryption key data and network identification data.

16. The computer-accessible medium of claim 15, the executable instructions further comprising executable instructions to perform:
upon the condition in which the wired connection is established, sending wireless communication configuration data from the computer to the portable X-ray detector for subsequent use in the wireless connection.

17. The computer-accessible medium of claim 16, further comprising:
signaling to the computer that the portable X-ray detector will be removed from a docking station and that the wired connection will be severed and subsequent wireless communication is expected between the portable X-ray detector and the computer.

18. The computer-accessible medium of claim 15, the executable instructions further comprising executable instructions to perform:
upon the condition in which the wired connection is established, sending image data from the portable X-ray detector to the computer.

* * * * *